United States Patent [19]
Cawood

[11] Patent Number: 6,045,542
[45] Date of Patent: Apr. 4, 2000

[54] URINE COLLECTION DEVICE

[75] Inventor: Charles D. Cawood, Houston, Tex.

[73] Assignee: Cawood Family Limited Partnership, Houston, Tex.

[21] Appl. No.: 09/229,799

[22] Filed: Jan. 13, 1999

[51] Int. Cl.⁷ ...................................................... A61B 1/00
[52] U.S. Cl. .......................................... 604/327; 604/544
[58] Field of Search .................................... 604/327, 328, 604/329, 345, 544, 324, 512; 128/DIG. 24

[56] References Cited

U.S. PATENT DOCUMENTS

| | | | |
|---|---|---|---|
| 2,612,895 | 10/1952 | Magee | 604/327 |
| 2,900,979 | 8/1959 | Bishop | 604/327 |
| 3,672,372 | 6/1972 | Heimlich | 604/544 |
| 3,721,243 | 3/1973 | Hesterman et al. . | |
| 3,897,785 | 8/1975 | Barto, Jr. | 604/327 |
| 3,943,929 | 3/1976 | Patel | 604/544 |
| 4,224,610 | 9/1980 | Quinby . | |
| 4,230,115 | 10/1980 | Walz et al. . | |
| 4,306,976 | 12/1981 | Bazzato . | |
| 4,449,971 | 5/1984 | Cawood | 604/544 |
| 4,581,763 | 4/1986 | Olsen . | |
| 5,234,420 | 8/1993 | Horton et al. | 604/345 |
| 5,496,300 | 3/1996 | Hirsch et al. | 604/327 |
| 5,531,724 | 7/1996 | Young et al. | 604/327 |

Primary Examiner—Wynn Wood Coggins
Assistant Examiner—A. T. Nguyen
Attorney, Agent, or Firm—Tilton, Fallon, Lungmus & Chestnut

[57] ABSTRACT

A flat urinary drainage bag that can be worn by a patient over the abdomen with the bag suspended from a waist-encircling belt is disclosed. The device includes an inlet tube for connection to a urethral catheter and a valve-equipped drain tube that extends downwardly from the bag when the drain tube is used to drain the contents therefrom. The lower end of the bag is foldable upwardly to position the drain tube in an upwardly-facing raised position against the bag's front wall, and a retaining strap is located across the front wall for holding the drain tube in its raised position. Spot attachments that secure the ends of the strap to the bag's front wall also secure the front and rear walls of the bag together, thereby performing multiple functions of limiting bulging of the bag in use, reducing sloshing of the bag's contents, and securing the retaining strap (and the raised drainage tube) in place.

5 Claims, 1 Drawing Sheet

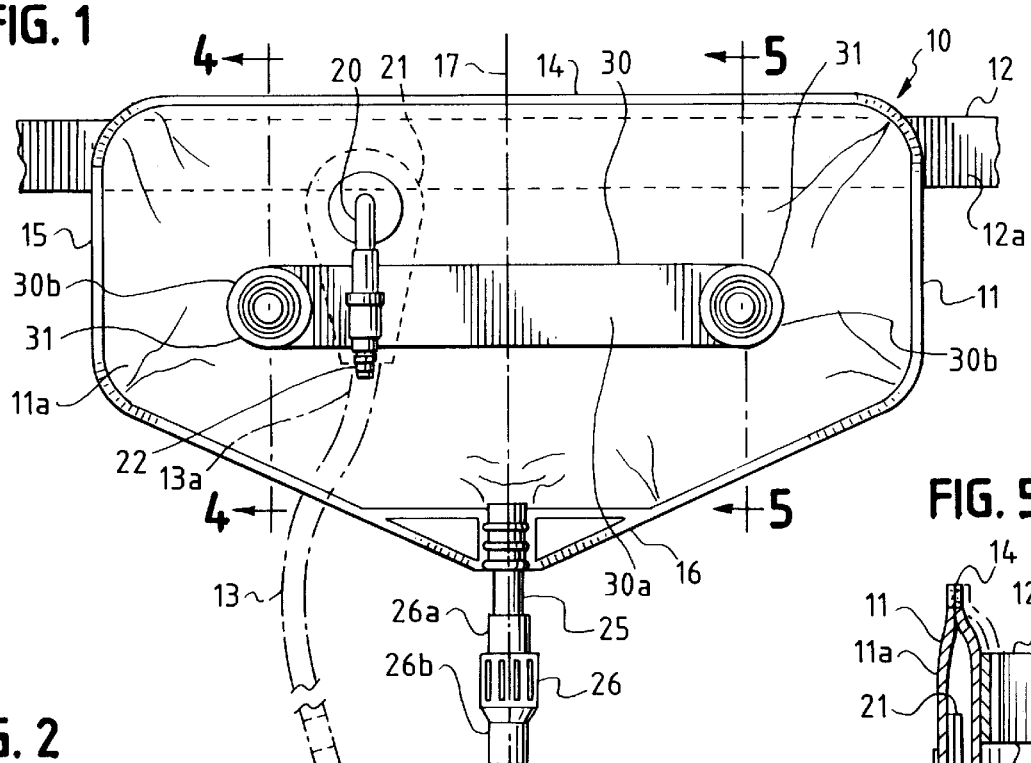
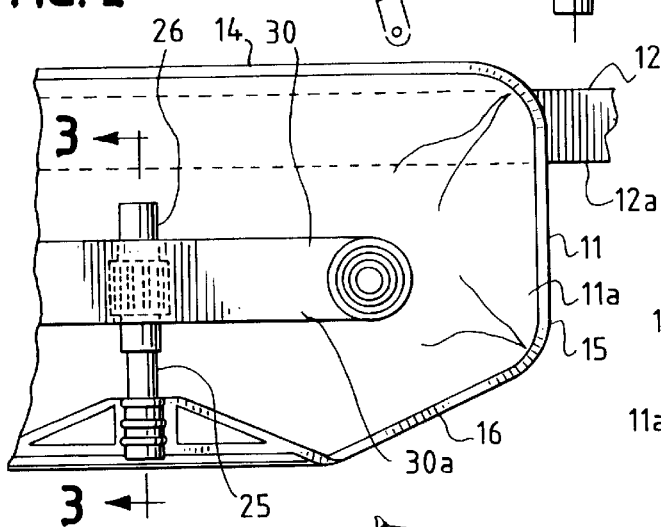
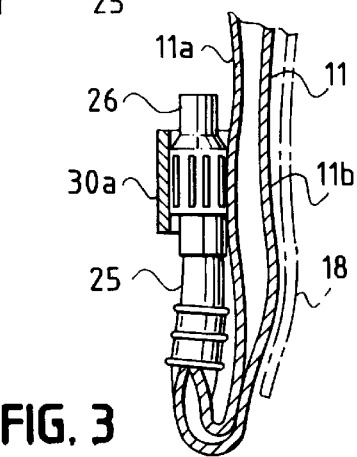
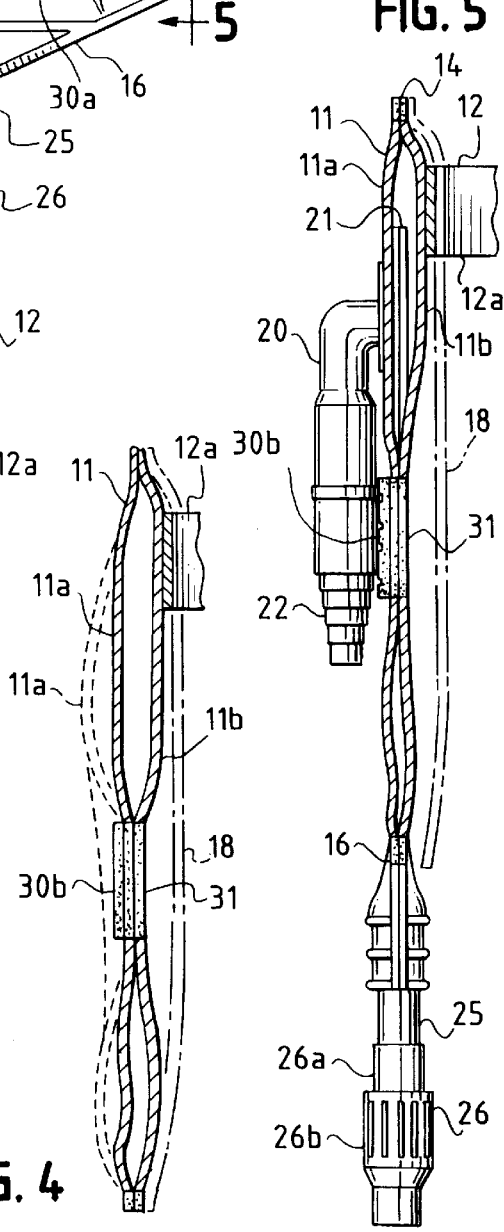

URINE COLLECTION DEVICE

BACKGROUND AND SUMMARY

Conventional urinary drainage bags are commonly strapped to a patient's leg above the knee, as disclosed in Barto U.S. Pat. No. 3,897,785, so that urine will flow into the bag under the influence of gravity. For an ambulatory patient, such an arrangement is often inconvenient and uncomfortable because, as such a bag becomes filled with urine, there is a tendency for it to slide downwardly along the leg unless additional means are provided on the bag to restrain such sliding movement. Also, such leg bags may be conspicuous through clothing as the bags become filled and may be awkward to drain.

Cawood U.S. Pat. No. 4,449,971 discloses that gravity flow is not essential for purposes of filling a urine collection bag. Intrinsic bladder detrusor muscle tone and intraperitoneal pressures exerted upon the bladder of a catheterized ambulatory patient will cause urine to flow from the bladder to a level as high as 10 centimeters or more above the distal tip of the catheter. A highly effective urinary drainage system may therefore be provided for an ambulatory patient in which the collection bag is carried by a waistband or belt and is worn over the patient's abdomen instead of along the inside of the leg.

The bag disclosed in the Cawood patent has a short valve-equipped drain tube that extends downwardly from the bag when the contents are to be drained and that may be folded upwardly and inserted into a pocket provided by the bag when the drain tube is not in use. A central heat seal joins the front and rear wall of the bag to cause more uniform distribution of fluid within the bag and reduce audible splashing of the contents when sudden body movements occur.

A main aspect of this invention is to provide an improved bag to be worn over the abdomen in which the retaining means for holding the drainage tube in raised condition against the front wall of the bag takes the form of a flexible transverse strap. Spot welds not only join the end portions of the strap to the bag's front wall but also provide laterally-spaced zones of interconnection between the bag's front and back walls, thereby effectively reducing sloshing of the contents during body movement, limiting the bulging of the bag when filled, and securing the strap in its position to function as means for holding the drain tube in its raised position. Because the strap is effectively welded at its end portions to both of the walls of the bag, the zones of connection are effectively reinforced against tearing and the possibilities are reduced that the front wall might be deformed or distorted by any pulling force transmitted by the strap.

The heat seals or zones of interconnection are circular in outline with each interconnection being located substantially midway between the bag's vertical midline and one of its side edges. The drain tube is located along the bag's midline and, when in raised condition, its valve-equipped end portion is tucked between the bag's front wall and the central portion of the flexible retaining strap.

An inlet tube is joined to the front wall of the bag above the drain tube and is adapted to be connected to a urethral catheter. A one-way inlet valve communicates with the inlet tube for preventing the flow of urine in a reverse direction. When the bag is worn, the distal tip of the catheter will normally be located above 5 to 10 centimeters below the inlet of the bag; however, intrinsic detrusor muscle tone of the bladder and intraperitoneal pressures associated with common body action such as walking, bending, and breathing result in fluid flow from the bladder into the bag with the anti-refluxing valve preventing reverse flow through the catheter.

Other features, advantages, and objects of the invention will become apparent from the drawings and specification.

DRAWINGS

FIG. 1 is a front elevational view of a urine collection device embodying the invention.

FIG. 2 is a framentary front elevational view similar to FIG. 1 but showing the drain tube retained in its raised position.

FIG. 3 is an enlarged fragmentary sectional view taken along line 3—3 of FIG. 2.

FIG. 4 is an enlarged vertical sectional view taken along line 4—4 of FIG. 1.

FIG. 5 is an enlarged vertical sectional view taken along line 5—5 of FIG. 1.

DETAILED DESCRIPTION OF PREFERRED EMBODIMENT

Referring to the drawings, the numeral 10 generally designates a urine collection device comprising an abdominal bag 11, a belt 12 for supporting the bag about a wearer's waist, and a catheter 13 for conveying urine from the bladder to the collection bag. In use, the bag would be worn as shown and described in aforementioned U.S. Pat. No. 4,449,971, the disclosure of which is incorporated by reference herein.

The bag 11 is substantially flat when empty and is dimensioned to extend over a patient's abdomen or belly. The front and rear walls 11a and 11b of the bag are joined together along their top, side and bottom edges 14, 15 and 16, respectively. Top edge 14 is generally straight and extends horizontally when the bag is worn. The walls of the bag may be formed of any suitable thermoplastic film that is tough, flexible, and liquid/gas impermeable. As indicated in the drawings, the edges 14–16 are preferably heat sealed together. The bottom edge 16 is generally V-shaped in outline with its side sections sloping downwardly toward the bag's vertical midline 17.

The bag may optionally include a soft, flexible rear panel 18, which may be flocked or non-woven fabric, and is shown only in phantom in FIGS. 3–5. The rear panel, serves as a comfort panel to keep the bag from sticking to a patient's skin, and is preferably joined to rear wall 11b by the same peripheral heat seal extending along edges 14–16. Belt 12 may be secured to rear wall 11b by any suitable means. Where a rear comfort panel is provided, the strap portions 12a of the belt may extend outwardly through vertical slits (not shown) in rear panel 18, in which case direct attachment of the belt to rear wall 11b becomes unnecessary since the rear panel 18 then serves to join the belt and bag together.

An inlet tube 20 formed of polyvinyl chloride or other suitable thermoplastic material is heat sealed to the upper front wall 11a of the bag and communicates in the interior of the bag to a suitable one-way valve 21. As shown in FIG. 1, the exterior portion of the inlet tube is operatively connected to the proximal end 13a of catheter 13. The connection might be a permanent one, although a separable connection is preferred. To facilitate coupling and uncoupling of the catheter and inlet tube and at the same time achieve a secure connection that will not become accidentally disrupted, it has been found desirable to seal a connecting sleeve or nipple 22 to the outer end of the inlet tube, the nipple being stepped as shown and being formed of a relatively rigid material such as, for example, polystyrene.

The one-way valve may be formed of a pair of flexible thermoplastic strips heat sealed along their edges to define a passage communicating at one end with inlet tube 20 and open at its other end only when fluid pressure within the passage forces the strips apart, thereby functionally as an anti-refluxing flap valve.

A short drain tube 25 formed of polyvinyl chloride or other flexible thermoplastic material is heat sealed to the lower edges of the bag and communicates with the bag's interior. At its free end, the drain tube is equipped with a suitable valve 26. The particular valve depicted in the drawings is composed of two elements 26a and 26b that are threadedly connected to each other. Opening and closing of the valve is achieved simply by rotating element 26b one way or the other with respect to element 26a. Since such a valve is entirely conventional and well known for use in collection appliances, a more detailed discussion of its structure and operation is believed unnecessary.

Drain tube 25 is located along the bag's vertical midline 17 as shown most clearly in FIG. 1. In that view, as well as in FIG. 5, the drain tube 25 is shown extending downwardly in the position it would assume if a patient wished to drain fluid from the bag. When valve 26 is closed, the bag might conceivably be worn with the drain tube extending downwardly; however, to provide greater patient comfort and to protect the tube and its valve against contact that might result in unintentional opening of the valve, it is preferable that the bag normally be worn with the drain tube in its raised position depicted in FIGS. 2 and 3. The tapered lower portion of the bag is simply folded upwardly to position the drain tube 25 against the front wall 11a and along the bag's vertical midline 17.

Retention means are provided in the form of flexible strap 30. The elongated strap extends transversely (horizontally) and includes central portion 30a and end portions 30b. Circular heat seals 31 not only join the end portions 30b to the front wall of the bag but also secure together the front and rear walls 11a and 11b at two laterally-spaced zones of attachment. It will be observed that the two spots or zones of interconnection are spaced equal distances on opposite sides of the vertical midline 17 and that each heat seal 31 is located approximately midway between midline 17 and a side edge 15.

The strap 30 is located so that when the drain tube 25 is in its raised position the valve 26 will be at approximately the same elevation as the strap and may be tucked between front wall 11a and the central portion 30a of the strap (FIGS. 2 and 3).

The dimensions of the bag may be varied depending on the size of the patient. In general, the bag should have a width within the range of about 20 to 40 centimeters (preferably about 30 centimeters) and a height of about 10 to 20 centimeters (preferably about 15 centimeters), excluding the length of drain tube 25 and its valve 26. In any event, the bag should be dimensioned to extend generally over the wearer's abdomen, from his (her) waist down to the pelvic region. When the bag is so worn, it is positioned at approximately the same height as the wearer's bladder.

It is to be understood that the appliance is useful for both male and female patients. In both cases, the intrinsic bladder detrusor muscle tone and the intraperitoneal pressure created during normal body movements or actions, such as breathing, walking, and bending, provide sufficient pressure to direct urine upwardly through the short length of catheter 13 and into the inlet tube 20 and one-way valve 21 in the upper portion of the collection bag 11. Therefore, despite the fact that the urine collection bag is carried by a belt or waistband over the patient's abdomen, urine from the bladder is readily directed into the bag. Reverse flow, especially as might otherwise occur if the patient were sitting or reclining, is prevented by the anti-refluxing flap valve 21.

While in the foregoing, an embodiment of the invention has been described in detail for purposes of illustration, it will be understood by those skilled in the art that many of these details may be varied without departing from the spirit and scope of the invention.

What is claimed is:

1. A urine collection device comprising a flat bag adapted to be worn by a patient across the abdomen, said bag having front and rear walls of flexible thermoplastic joined to each other along top, bottom, and side edges to define a urine-receiving chamber; support means for supporting said bag from a patient's waist; a valve-equipped drain tube located along said bottom edge and communicating with the interior of said bag; an inlet tube joined to said front wall above said drain tube and adapted to be connected to a urethral catheter; a one-way inlet valve communicating with said inlet tube for preventing flow in a reverse direction therethrough; said drain tube extending downwardly from said bottom edge when said drain tube is being used to drain the contents from said bag but being foldable upwardly into raised position against said front wall when said drain tube is not in use; and retaining means for holding said drain tube in its raised position; wherein the improvement comprises said retaining means being in the form of a flexible strap traversing a mid-section of said front wall; said strap having a central portion and a pair of opposite end portions; and attachment means joining said end portions of said strap to said front wall; said attachment means also connecting said front and rear walls together to limit bulging of said bag and sloshing of its contents when said device is worn.

2. The device of claim 1 in which said attachment means comprises a pair of spot heat seals fusing said strap end portions, said front wall, and said rear wall together at two spaced zones of interconnection.

3. The device of claim 2 in which said zones of interconnection are circular in outline and are spaced equidistant from the vertical midline of said bag.

4. The device of claim 3 in which said drain tube extends along said midline of said bag and between said central portion of said strap and said front wall when said drain tube is in raised position and is retained by said strap.

5. The device of claim 3 in which each zone of interconnection is located substantially midway between said midline and a side edge of said bag.

* * * * *